United States Patent
Ukawa

(10) Patent No.: US 9,566,008 B2
(45) Date of Patent: Feb. 14, 2017

(54) BIOLOGICAL SIGNAL PROCESSING APPARATUS AND MEDICAL APPARATUS CONTROLLING METHOD

(75) Inventor: Teiji Ukawa, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 767 days.

(21) Appl. No.: 12/878,325

(22) Filed: Sep. 9, 2010

(65) Prior Publication Data
US 2011/0060714 A1 Mar. 10, 2011

(30) Foreign Application Priority Data

Sep. 9, 2009 (JP) ................................. 2009-208516

(51) Int. Cl.
| G06N 5/02 | (2006.01) |
| A61B 5/021 | (2006.01) |
| G06N 7/00 | (2006.01) |
| A61B 5/0402 | (2006.01) |
| A61B 5/00 | (2006.01) |

(52) U.S. Cl.
CPC ............. *A61B 5/021* (2013.01); *A61B 5/0402* (2013.01); *A61B 5/7275* (2013.01); *G06N 7/005* (2013.01)

(58) Field of Classification Search
None
See application file for complete search history.

(56) References Cited

U.S. PATENT DOCUMENTS

| 5,263,487 | A | * | 11/1993 | Sakamoto et al. | A61B 5/04002 600/544 |
| 5,737,488 | A | * | 4/1998 | Iso | G10L 15/142 704/255 |
| 5,752,920 | A | | 5/1998 | Ogura et al. | |
| 6,658,287 | B1 | | 12/2003 | Litt et al. | |
| 7,539,532 | B2 | * | 5/2009 | Tran | A61B 5/021 600/509 |
| 7,539,533 | B2 | * | 5/2009 | Tran | A61B 5/0022 600/509 |

(Continued)

FOREIGN PATENT DOCUMENTS

| JP | 2002-288758 A | 10/2002 |
| JP | 2003-517320 A | 5/2003 |

(Continued)

OTHER PUBLICATIONS

Japanese Office Action for related Japanese Patent Application No. 2009-208516 dated Feb. 7, 2012.

(Continued)

*Primary Examiner* — Kakali Chaki
*Assistant Examiner* — Fuming Wu
(74) *Attorney, Agent, or Firm* — Kenealy Vaidya LLP

(57) ABSTRACT

A biological signal processing apparatus includes: a provider which provides state probability which corresponds to a value of a first biological signal; an acquirer which acquires a first biological signal in time series from a living body and which acquires state probability in time series which corresponds to a value of the acquired first biological signal from the provider; and a determiner which acquires determination probability based on the state probability acquired by the acquirer and which performs determination whether a process is performed or not by using the determination probability.

10 Claims, 22 Drawing Sheets

(56) References Cited

U.S. PATENT DOCUMENTS

| | | | |
|---|---|---|---|
| 7,733,224 B2 * | 6/2010 | Tran | G06F 19/3418 340/3.1 |
| 8,108,036 B2 * | 1/2012 | Tran | A61B 5/0022 600/509 |
| 8,200,321 B2 * | 6/2012 | McCombie | A61B 5/0002 600/301 |
| 2006/0241708 A1 * | 10/2006 | Boute | A61B 5/0452 607/17 |
| 2006/0282021 A1 * | 12/2006 | DeVaul | A61B 5/0024 600/595 |
| 2007/0150024 A1 * | 6/2007 | Leyde | A61B 5/0476 607/45 |
| 2007/0287931 A1 * | 12/2007 | Dilorenzo | A61B 5/0476 600/545 |
| 2008/0114219 A1 * | 5/2008 | Zhang | A61B 5/02055 600/301 |
| 2008/0188763 A1 * | 8/2008 | John | A61B 5/0452 600/516 |
| 2008/0214904 A1 * | 9/2008 | Saeed | A61B 5/0006 600/301 |
| 2008/0269625 A1 | 10/2008 | Halperin et al. | |
| 2008/0294033 A1 * | 11/2008 | Yamazaki | A61B 5/0478 600/407 |
| 2010/0280809 A1 | 11/2010 | Takahashi et al. | |
| 2010/0298650 A1 * | 11/2010 | Moon | A61B 5/0002 600/301 |
| 2010/0298653 A1 * | 11/2010 | McCombie | A61B 5/0002 600/301 |
| 2010/0298654 A1 * | 11/2010 | McCombie | A61B 5/0002 600/301 |
| 2011/0060714 A1 * | 3/2011 | Ukawa | A61B 5/021 706/52 |

FOREIGN PATENT DOCUMENTS

| | | |
|---|---|---|
| JP | 3054084 B2 | 4/2004 |
| JP | 3817586 B2 | 6/2006 |
| JP | 2008-543478 A | 12/2008 |
| WO | 2006/136972 A1 | 12/2006 |
| WO | 2008/075288 A2 | 6/2008 |
| WO | 2009/054351 A1 | 4/2009 |

OTHER PUBLICATIONS

Extended European Search Report dated Nov. 22, 2010 for EP 10 17 5343.

Japanese Office Action for related Japanese Patent Application No. 2009-208516 dated Oct. 3, 2012.

* cited by examiner

FIG. 2

| MEASURED VALUE OF SpO2 | LOW-OXYGEN STATE PROBABILITY | PROBABILITY AT WHICH LOW-OXYGEN STATE IS NOT PRODUCED |
|---|---|---|
| 95% OR MORE | 0.0 | 1.0 |
| 94% | 0.1 | 0.9 |
| 93% | 0.2 | 0.8 |
| 92% | 0.3 | 0.7 |
| 91% | 0.4 | 0.6 |
| 90% | 0.5 | 0.5 |
| 89% | 0.6 | 0.4 |
| 88% | 0.7 | 0.3 |
| 87% | 0.8 | 0.2 |
| 86% | 0.9 | 0.1 |
| 85% OR LESS | 1.0 | 0.0 |

FIG. 8

| MEASURED VALUE OF BLOOD PRESSURE | LOW-BLOOD PRESSURE STATE PROBABILITY | PROBABILITY AT WHICH LOW-BLOOD PRESSURE STATE IS NOT PRODUCED |
|---|---|---|
| 100mmHg OR MORE | 0.0 | 1.0 |
| 99mmHg | 0.05 | 0.95 |
| 98mmHg | 0.1 | 0.9 |
| 97mmHg | 0.15 | 0.85 |
| 96mmHg | 0.2 | 0.8 |
| 95mmHg | 0.25 | 0.75 |
| 94mmHg | 0.3 | 0.7 |
| 93mmHg | 0.35 | 0.65 |
| 92mmHg | 0.4 | 0.6 |
| 91mmHg | 0.45 | 0.55 |
| 90mmHg | 0.5 | 0.5 |
| 89mmHg | 0.55 | 0.45 |
| 88mmHg | 0.6 | 0.4 |
| 87mmHg | 0.65 | 0.35 |
| 86mmHg | 0.7 | 0.3 |
| 85mmHg | 0.75 | 0.25 |
| 84mmHg | 0.8 | 0.2 |
| 83mmHg | 0.85 | 0.15 |
| 82mmHg | 0.9 | 0.1 |
| 81mmHg | 0.95 | 0.05 |
| 80mmHg OR LESS | 1.0 | 0.0 |

FIG. 23

| ESTIMATED BLOOD PRESSURE | LOW-BLOOD PRESSURE STATE PROBABILITY | PROBABILITY AT WHICH LOW-BLOOD PRESSURE STATE IS NOT PRODUCED |
|---|---|---|
| 90mmHg OR MORE | 0.0 | 1.0 |
| 89mmHg | 0.05 | 0.95 |
| 88mmHg | 0.1 | 0.9 |
| 87mmHg | 0.15 | 0.85 |
| 86mmHg | 0.2 | 0.8 |
| 85mmHg | 0.25 | 0.75 |
| 84mmHg | 0.3 | 0.7 |
| 83mmHg | 0.35 | 0.65 |
| 82mmHg | 0.4 | 0.6 |
| 81mmHg | 0.45 | 0.55 |
| 80mmHg | 0.5 | 0.5 |
| 79mmHg | 0.55 | 0.45 |
| 78mmHg | 0.6 | 0.4 |
| 77mmHg | 0.65 | 0.35 |
| 76mmHg | 0.7 | 0.3 |
| 75mmHg | 0.75 | 0.25 |
| 74mmHg | 0.8 | 0.2 |
| 73mmHg | 0.85 | 0.15 |
| 72mmHg | 0.9 | 0.1 |
| 71mmHg | 0.95 | 0.05 |
| 70mmHg OR LESS | 1.0 | 0.0 |

BIOLOGICAL SIGNAL PROCESSING APPARATUS AND MEDICAL APPARATUS CONTROLLING METHOD

BACKGROUND OF THE INVENTION

The present invention relates to a biological signal processing apparatus and medical apparatus controlling method which are suitable for causing a medical apparatus to perform a predetermined process such as a generation of an alarm, based on a biological signal.

Japanese Patent No. 3,817,586 discloses a related-art medical diagnostic apparatus in which a generation of an alarm is determined provided that a physiological parameter is stabilized, in order to avoid frequent generations of an alarm. Also JP-A-2003-517320 discloses a related-art alarm controlling method for a medical apparatus in which the amount of time when a measured value for a physiological parameter is past a threshold, and the degree at which the value is past a threshold are set as conditions.

Furthermore, Japanese Patent No. 3,054,084 discloses a related-art apparatus in which the blood pressure is measured provided that the pulse wave transit time (PWTT) exceeds a predetermined threshold.

In a related-art medical apparatus, as described above, whether a predetermined process is performed or not depends on whether the value of a biological signal exceeds a threshold or not. It is requested to develop a biological signal processing apparatus and medical apparatus controlling method in which an alarm generation and collection of biological signals can be performed more adequately correspondingly to the patient state.

SUMMARY

It is therefore an object of the invention to provide a biological signal processing apparatus and medical apparatus controlling method in which, in the case where a predetermined process such as a generation of an alarm based on a biological signal is performed, adequate determination can be made.

In order to achieve the object, according to the invention, there is provided a biological signal processing apparatus comprising: a provider which provides state probability which corresponds to a value of a first biological signal; an acquirer which acquires a first biological signal in time series from a living body and which acquires state probability in time series which corresponds to a value of the acquired first biological signal from the provider; and a determiner which acquires determination probability based on the state probability acquired by the acquirer and which performs determination whether a process is performed or not by using the determination probability.

The process may include a process of generating an alarm.

The process may include a process of returning from an alarm temporary eliminated state.

The process may include a process of acquiring a second biological signal.

The determiner may perform the determination by using a threshold.

The threshold may include an upper threshold and a lower threshold, and the determiner may perform the determination with hysteresis by using the upper threshold and the lower threshold.

The determiner may calculate the determination probability based on Bayes's theorem.

The biological signal processing apparatus may further include: a display; and a display controller which displays the determination probability acquired by the determiner on the display.

The biological signal processing apparatus may further include: a corrector which corrects the state probability acquired by the acquirer based on a second biological signal which is identical with or different from the first biological signal.

According to the invention, there is also provided a method of controlling a medical apparatus, the method comprising: acquiring a first biological signal in time series from a living body and acquiring state probability in time series which corresponds to a value of the acquired first biological signal; and acquiring determination probability based on the acquired state probability and performing determination whether a process is performed or not by using the determination probability.

The process may include a process of generating an alarm.

The process may include a process of returning from an alarm temporary eliminated state.

The process may include a process of acquiring a second biological signal.

The determination may be performed by using a threshold.

The threshold may include an upper threshold and a lower threshold, and the determination may be performed with hysteresis by using the upper threshold and the lower threshold.

The determination probability may be calculated based on Bayes's theorem.

The method may further include: displaying the determination probability.

The method may further include: correcting the acquired state probability based on a second biological signal which is identical with or different from the first biological signal.

BRIEF DESCRIPTION OF THE DRAWINGS

FIG. 2 is a view showing a comparison table of state probability and the value of a biological signal used in the first embodiment of the biological signal processing apparatus of the invention.

FIG. 8 is a view showing a comparison table of the state probability and the value of a biological signal used in a second embodiment of the biological signal processing apparatus of the invention.

FIG. 23 is a view showing a comparison table of the state probability and the value of a biological signal used in the fifth embodiment of the biological signal processing apparatus of the invention.

DETAILED DESCRIPTION OF EMBODIMENTS

Figure 1:
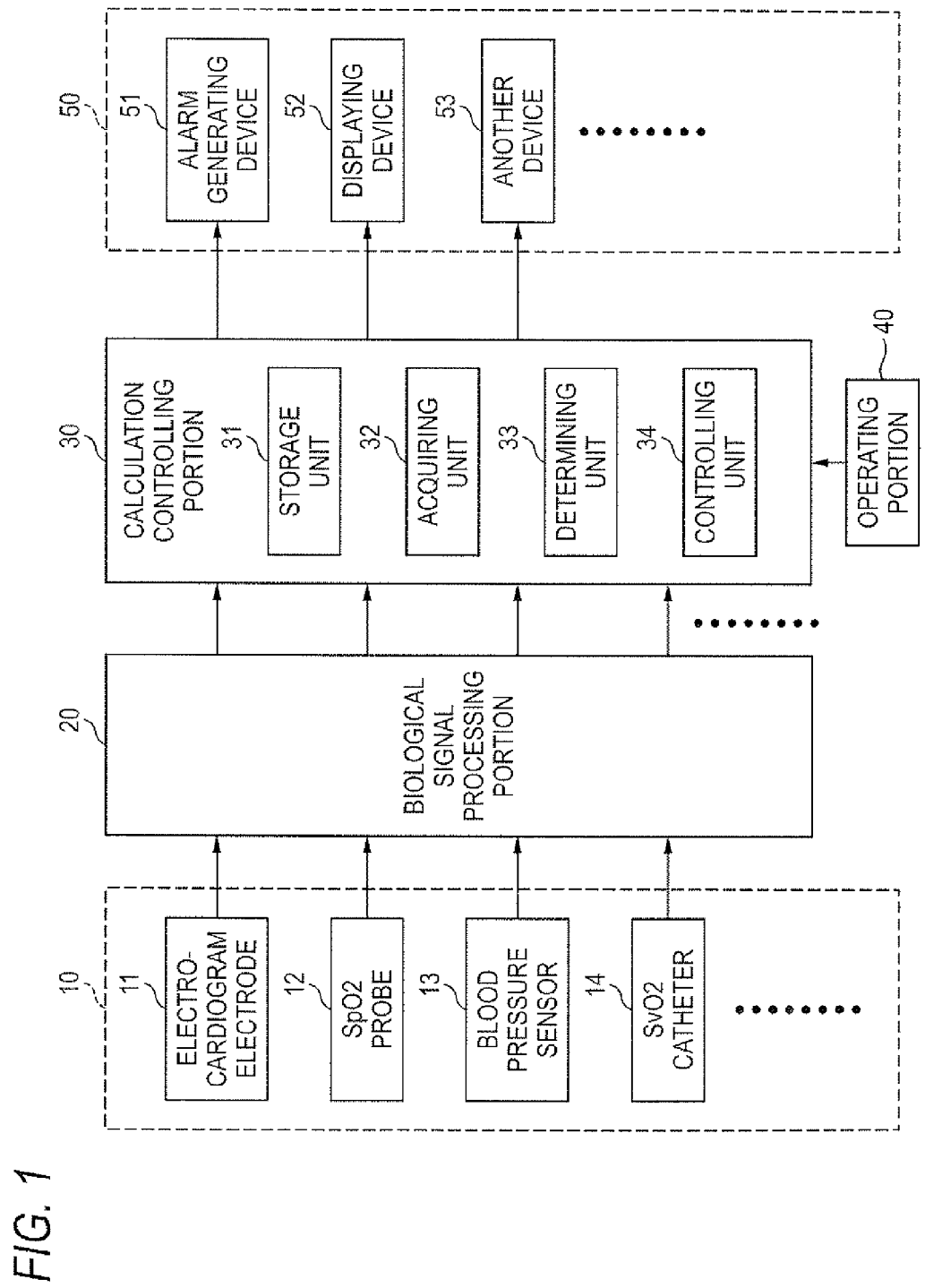
FIG. 1 is a diagram showing a first embodiment of the biological signal processing apparatus of the invention.

Hereinafter, embodiments of the biological signal processing apparatus and medical apparatus controlling method of the invention will be described with reference to accompanying drawings. In figures, identical components are denoted by the same reference numerals, and duplicate description will be omitted. FIG. 1 is a diagram of a medical apparatus in which a biological signal processing apparatus of an embodiment of the invention is used.

A sensor portion 10 includes electrocardiogram electrodes 11, an SpO2 probe 12, a blood pressure sensor 13, and an SvO2 catheter 14. The sensor portion 10 sends biological signals to a biological signal processing portion 20. The biological signal processing portion 20 receives the biological signals sent from the sensor portion 10, processes the biological signals into a heart rate, an ECG (Electrocardiogram) signal, an SpO2 (oxygen saturation), a blood pressure, and an SvO2 (mixed venous oxygen saturation) which are signals which a computer can process, and then sends the processed signals to a calculation controlling portion 30.

The calculation controlling portion 30 is configured by, for example, a computer, produces images for displaying waveforms and numerical values such as an electrocardiogram, the SpO2, the blood pressure, and the SvO2, by using the heart rate, the ECG signal, the SpO2, the blood pressure, the SvO2, displays the images on a displaying device 52, and controls a predetermined process, i.e., a process of generating an alarm. In order to perform these processes, the calculation controlling portion 30 includes a storage unit 31, an acquiring unit 32, a determining unit 33, and a controlling unit 34.

The storage unit 31 provides state probability of the living body state which corresponds to, in advance, each value of a biological signal which is divided into a predetermined width. The storage unit 31 stores a probability table in which the state probability of the living body state and the values of the biological signal correspond to each other in advance. In the embodiment, as shown in FIG. 2, the probability at which a low-oxygen state is produced (the low-oxygen state probability) and that at which a low-oxygen state is not produced are stored correspondingly to a value of the SpO2. In this example, the probability is evenly (linearly) changed every 1%. Alternatively, the probability may not be linearly changed.

The acquiring unit 32 acquires the state probability corresponding to a value of a biological signal which is acquired in time series from a living body, based on the probability table of the storage unit 31. The determining unit 33 acquires determination probability at which it is determined whether a predetermined process is performed or not, based on the state probability acquired in time series by the acquiring unit 32, and performs a determination by using the determination probability.

Here, the determining unit 33 acquires severity determination probability $P(t)$ of the patient from Expression 1 below. In the expression, $Ps(t)$ shows the low-oxygen state probability corresponding to the value (St) of the SpO2 at time t. The severity determination probability P(t) is a recurrence expression, and P(t−1) shows severity determination probability which is acquired by using the value of the SpO2 in the previous sampling. Expression 1 is an expression based on Bayes's theorem.

$$P(t)=P(t-1)\times Ps(t)/\{P(t-1)\times Ps(t)+(1-P(t-1))\times(1-Ps(t))\} \quad (\text{Exp. 1})$$

The determining unit 33 compares the severity determination probability P(t) with a threshold, and determines whether an alarm is generated or not. In the embodiment, the threshold is configured by an upper threshold and a lower threshold so that the determination is provided with hysteresis. Specifically, 0.65 is employed as the upper threshold, and 0.35 is employed as the lower threshold. However, the provision of hysteresis is not essential, and alternatively the determination may be performed by using a single threshold.

The controlling unit 34 controls an alarm generation of an alarm generating device 51 included in an output device portion 50, based on a result of the determination of the determining unit 33.

The output device portion 50 includes the alarm generating device 51, a displaying device 52, and another device 53. The alarm generating device 51 includes a speaker for generating an alarm. The displaying device 52 is a monitor device including an LCD. The other device 53 indicates other outputting devices such as a printer and a communicating device.

Figure 3:
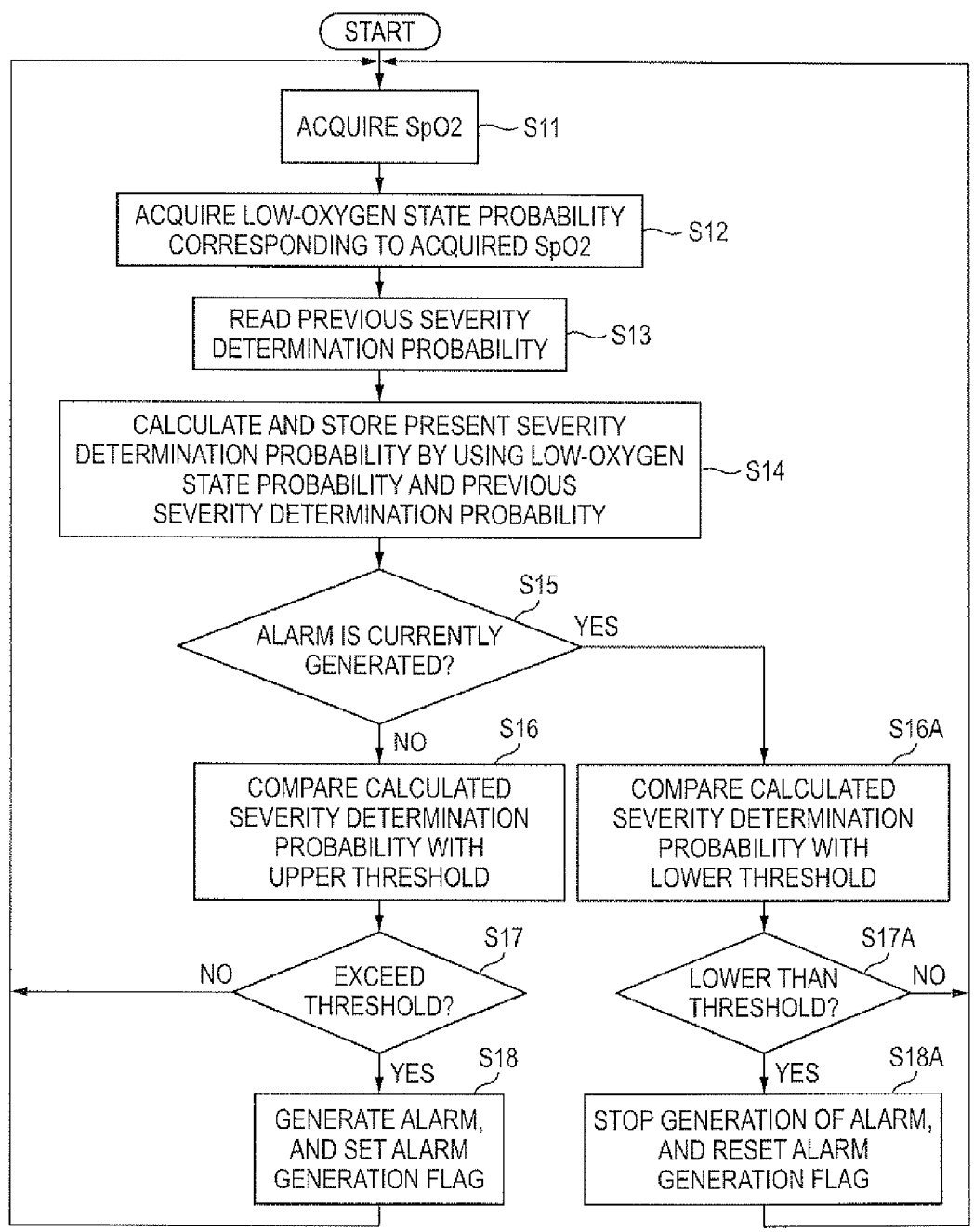
FIG. 3 is a flowchart showing the operation of the first embodiment of the biological signal processing apparatus of the invention.

In the thus configured medical apparatus, on the basis of the program of the flowchart shown in FIG. 3, the calculation controlling portion 30 functioning as the acquiring unit 32, the determining unit 33, and the controlling unit 34 performs a process, and therefore the operation will be described with reference to the flowchart.

When the medical apparatus is powered ON, for example, the operation is started, and in this case the SpO2 is acquired as a biological signal (S11). The calculation controlling portion 30 acquires the low-oxygen state probability Ps corresponding to the acquired SpO2, from the table which is stored in the storage unit 31, and which is shown in FIG. 2 (S12 (the acquiring unit 32)).

Then, the calculation controlling portion 30 reads the stored previous severity determination probability (S13), calculates the present severity determination probability P(t), on the basis of Expression 1 above by using the low-oxygen state probability Ps which is acquired in step S12, and the previous severity determination probability P(t−1), and stores the calculated probability in a predetermined register (S14 (the determining unit 33)). Furthermore, the calculation controlling portion 30 checks the flag to determine whether an alarm is currently generated or not (S15).

If it is detected in step S15 that an alarm is not currently generated, a comparison is made to check whether the present severity determination probability P(t) is larger than the upper threshold (0.65) or not (S16) to determine whether the probability is larger than the upper threshold (0.65) or not (S17). If it is detected in step S17 that the probability is larger than the upper threshold, the alarm generating device 51 is controlled so as to generate an alarm, and an alarm generation flag is set (S18). Then, the control returns to step S11. The steps following step S11 are repeated every one sampling.

If it is detected in step S17 that an alarm is currently generated, a comparison is made to check whether the present severity determination probability P(t) is smaller than the lower threshold (0.35) or not (S16A) to determine whether the probability is smaller than the lower threshold (0.35) or not (S17A). If it is detected in step S17A that the probability is smaller than the lower threshold, the alarm generating device 51 is controlled so as to stop the generation of an alarm, and reset the alarm generation flag (S18A). Then, the control returns to step S11. The steps following step S11 are repeated every one sampling.

Figure 4:
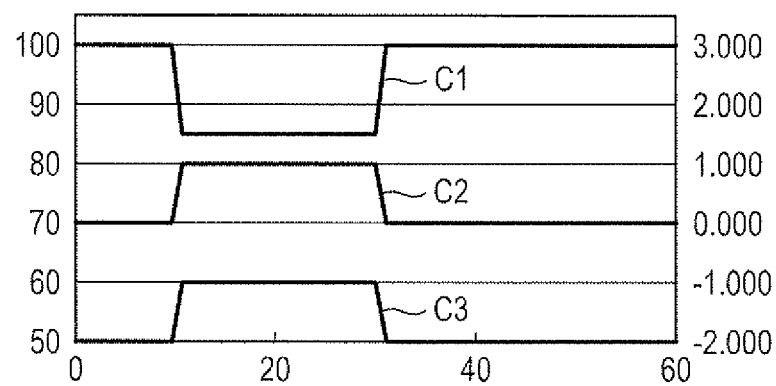
FIG. 4 is a view showing temporal changes of the biological signal, the state probability, and a generation of an alarm in the case where a process is performed in the first embodiment of the biological signal processing apparatus of the invention.

As a result of the above-described process, in the case where the SpO2 (%) indicated by C1 is measured, when the SpO2 (%) is rapidly decreased to 85% or less and thereafter this state is continued, as shown in FIG. 4, for example, the severity determination probability P(t) indicated by C2 is constantly maintained to 1, and an alarm is synchronously generated as indicated by C3. When the SpO2 (%) is thereafter increased and in accordance with this the severity determination probability P(t) is decreased to be lower than the lower threshold (0.35), the generation of the alarm is stopped.

Figure 5:
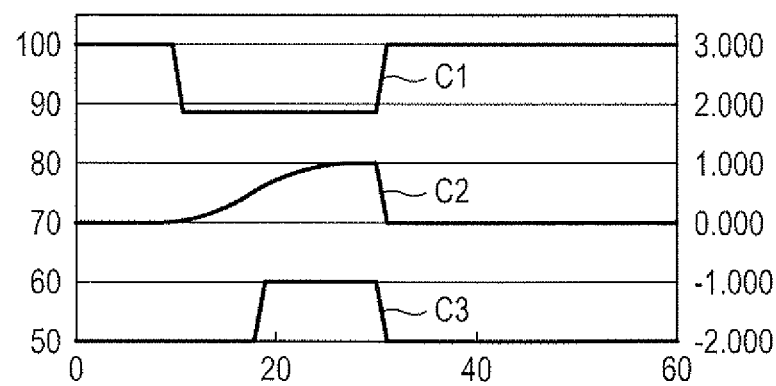
FIG. 5 is a view showing temporal changes of the biological signal, the state probability, and the generation of an alarm in the case where a process is performed in the first embodiment of the biological signal processing apparatus of the invention.

In the case where the SpO2 (%) indicated by C1 is measured, when the SpO2 (%) is decreased to 90% and thereafter this state is continued, as shown in FIG. 5, for example, the severity determination probability P(t) indicated by C2 is gradually increased, and, when the probability becomes larger than the upper threshold (0.65), an alarm generation indicated by C3 is performed from this timing. When the SpO2 (%) is thereafter increased and in accordance with this the severity determination probability P(t) is decreased to be lower than the lower threshold (0.35), the generation of the alarm is stopped.

Figure 6:
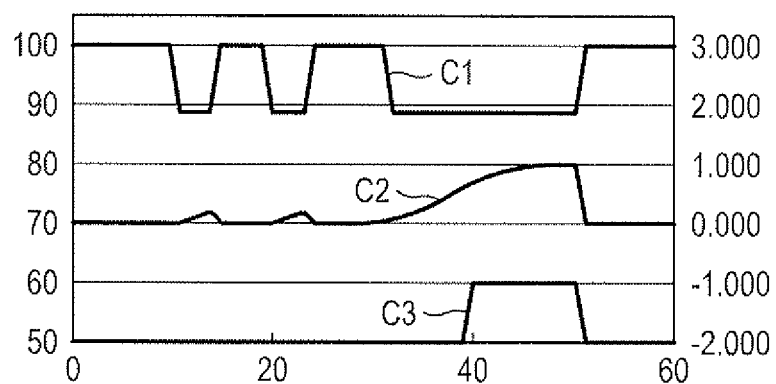
FIG. 6 is a view showing temporal changes of the biological signal, the state probability, and the generation of an alarm in the case where a process is performed in the first embodiment of the biological signal processing apparatus of the invention.

In the case where the SpO2 (%) indicated by C1 is measured, even when a change such as that in which the SpO2 (%) is decreased to 90% at a certain instant (at the timing of one sampling) and thereafter immediately increased occurs, as shown in FIG. 6, for example, the severity determination probability P(t) indicated by C2 is correspondingly slightly increased, but does not become larger than the upper threshold (0.65), and the alarm generation is not performed as indicated by C3. The change of the SpO2 (%) subsequent to this is identical with that described with reference to FIG. 5, and its description is omitted.

Figure 7:
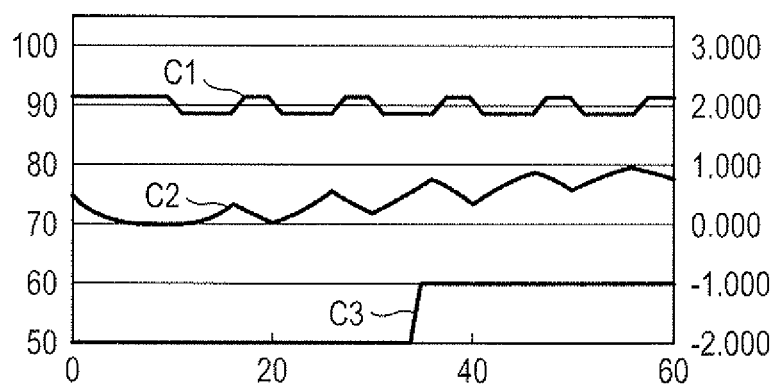
FIG. 7 is a view showing temporal changes of the biological signal, the state probability, and the generation of an alarm in the case where a process is performed in the first embodiment of the biological signal processing apparatus of the invention.

In the case where the SpO2 (%) indicated by C1 is measured, when the SpO2 (%) is continuously repeatedly changed between 91% and 89%, as shown in FIG. 7, for example, the severity determination probability P(t) indicated by C2 is correspondingly repeatedly changed while being continuously increased and decreased, and as a whole changed to be slightly increased with elapsed time. When the severity determination probability P(t) then becomes larger than the upper threshold (0.65), the alarm generation indicated by C3 is performed from this timing. Furthermore, the SpO2 (%) is continuously repeatedly increased and decreased. However, the severity determination probability P(t) is not decreased to be lower than the lower threshold (0.35), and hence the generation of the alarm is not stopped. Therefore, a tendentially severe situation is captured, and the generation of the alarm is continued, so that an adequate alarm generation is ensured.

In the examples of FIGS. 4 to 7, in the case where the threshold of the SpO2 (%) is 90%, when the SpO2 is larger than and smaller than the threshold, an alarm generation and a stop of alarm generation are repeated in the related art. In the embodiment, by contrast, a severe situation can be correctly detected, and an alarm generation and a stop of alarm generation are performed. This is preferable. In the related-art examples, even when two thresholds are used to provide hysteresis, the above-discussed problem of the related-art examples cannot be solved in the examples of FIGS. 4 to 6, and adequate two thresholds is hardly selected in the example of FIG. 7.

Figure 9:
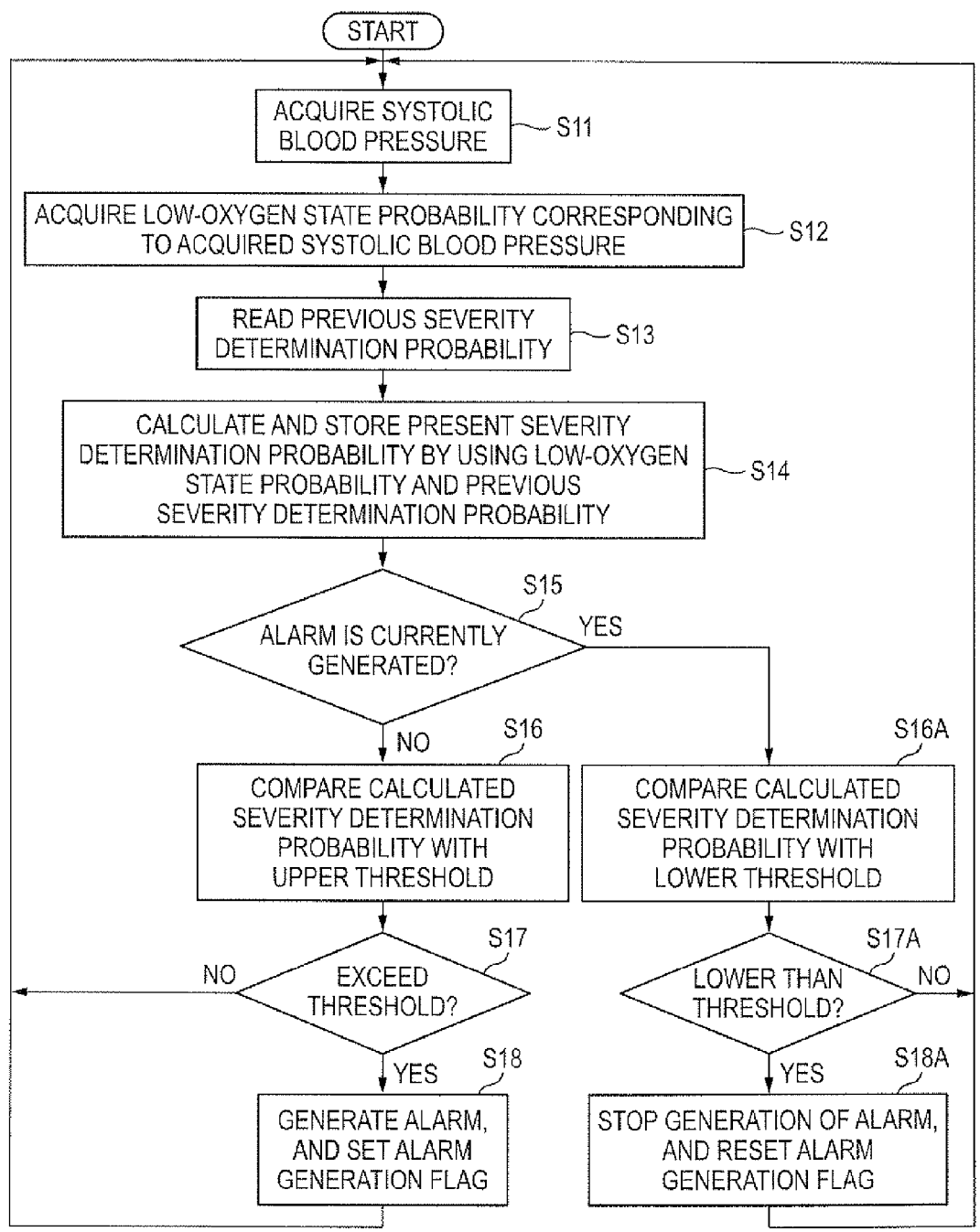
FIG. 9 is a flowchart showing the operation of the second embodiment of the biological signal processing apparatus of the invention.

In a second embodiment, in place of the SpO2 (%), the systolic blood pressure (hereinafter, referred to merely as the blood pressure) is acquired to acquire low-blood pressure state probability. Therefore, the storage unit 31 includes a table in which, as shown in FIG. 8, the low-blood pressure state probability of from 0.0 to 1.0 is correlated in steps of 0.05 with from 100 mmHg to 80 mmHg. FIG. 9 shows a flowchart of a process which is performed by a medical apparatus. The process is identical with the flowchart of FIG. 3 including the upper and lower thresholds except that the blood pressure is used in place of the SpO2 (%), and hence a description with reference to a flowchart is omitted.

Figure 10:
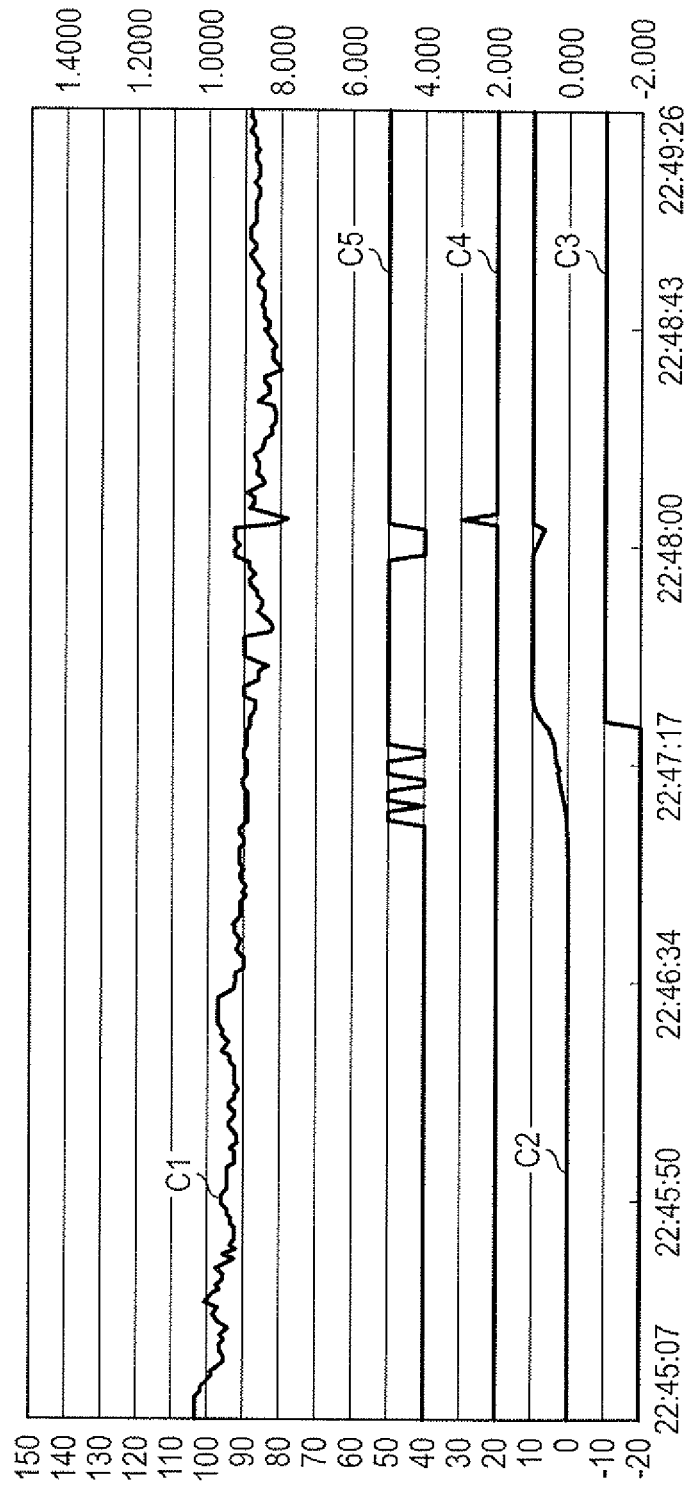
FIG. 10 is a view showing temporal changes of the biological signal, the state probability, and a generation of an alarm in the case where a process is performed in the second embodiment of the biological signal processing apparatus of the invention.

FIG. 10 is a view in which a change in the second embodiment between an alarm generation and a stop of an alarm generation is indicated by C3, and also a simple comparison of the blood pressure with 80 mmHg (threshold) in the related-art example, which is indicated by C4, and a simple comparison of the blood pressure with 90 mmHg (threshold) in the related-art example, which is indicated by C5 are shown. As shown in FIG. 10, when the blood pressure which is indicated by C1 is changed, an alarm generation and a stop of an alarm generation are frequently repeated in the simple comparison with 90 mmHg (threshold) which is indicated by C5. In the embodiment, by contrast, low-blood pressure determination probability which is produced from the low-blood pressure state probability by using Expression 1 above transits, and which is indicated by C2 transits, and hence repetition between an alarm generation and a stop of an alarm generation is suppressed, so that a series of generations of an alarm is performed. In the related-art example with 80 mmHg (threshold) which is indicated by C4, it is hardly determined to be severe. In the embodiment, it is earlier determined to be severe, and this situation is informed by an alarm generation.

In an operating portion 40 shown in FIG. 1, an alarm sound temporary stop switch (hereinafter, referred to merely as the temporary stop switch) is disposed, so that a medical person who recognizes an alarm generation can temporarily stop the alarm sound. In the case where, as shown in (a) of FIG. 11, an alarm generation and a stop of an alarm generation are frequently repeated (plural transitions occur), even when the temporary stop switch is operated at, for example, timing T1 of FIG. 11, a stop of the alarm generation is performed at T2, and hence the temporary stop is reset. When an alarm generation and a stop of the alarm generation are then repeated, an unintended alarm sound is emitted ((b) of FIG. 11).

Figure 11:
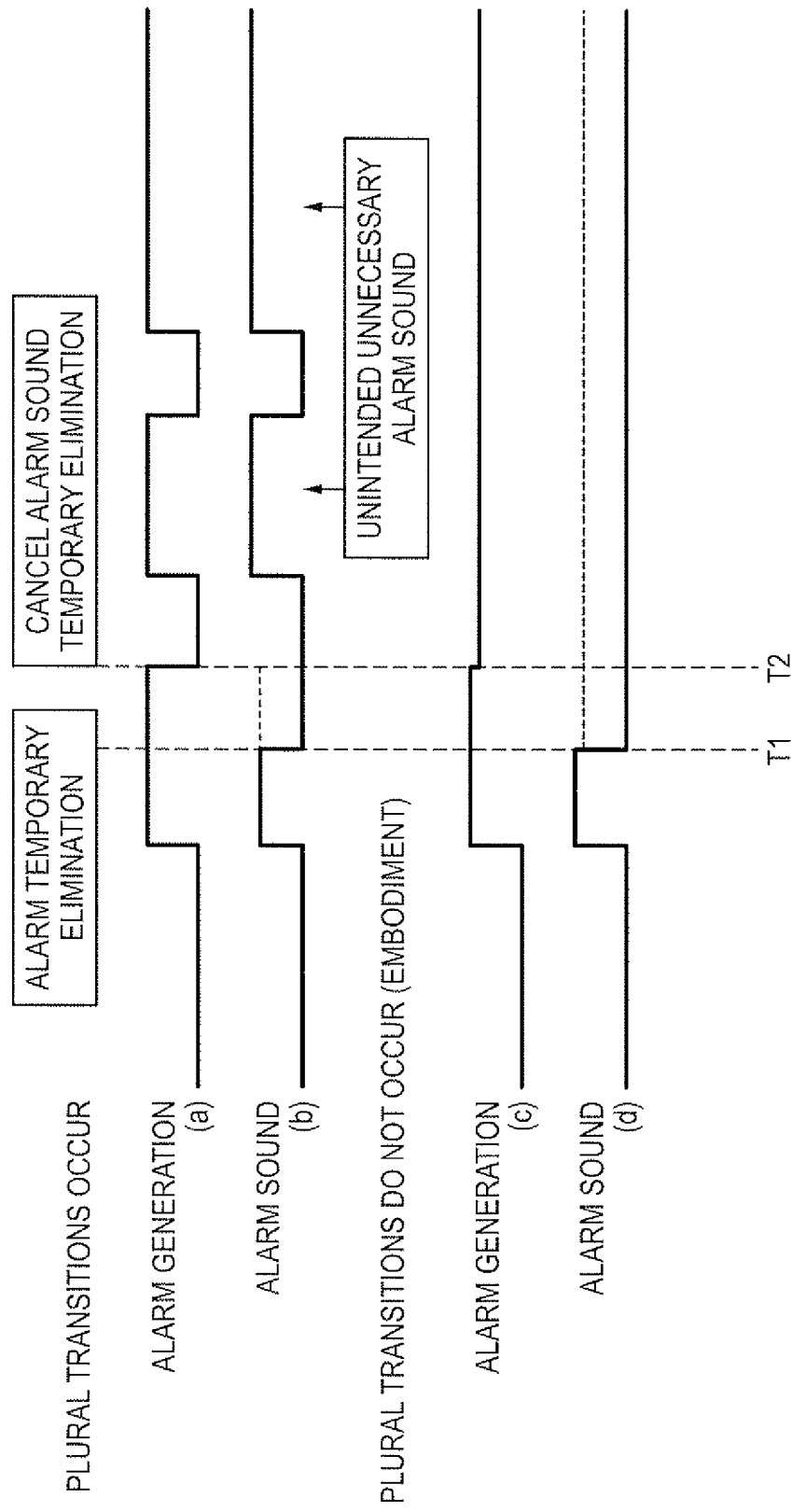
FIG. 11 is a view showing temporal changes in alarm sound temporary elimination in the case where a process is performed in the second embodiment of the biological signal processing apparatus of the invention, and in the case where a process is performed by a related-art technique.

According to the embodiment, by contrast, an alarm generation and a stop of an alarm generation are not repeated (plural transitions do not occur), and an alarm generation is performed one time ((c) of FIG. 11). When the temporary stop switch is operated at timing T1 of FIG. 11, therefore, the alarm sound is not emitted thereafter, and the temporary elimination can be continued as intended.

Figure 12:
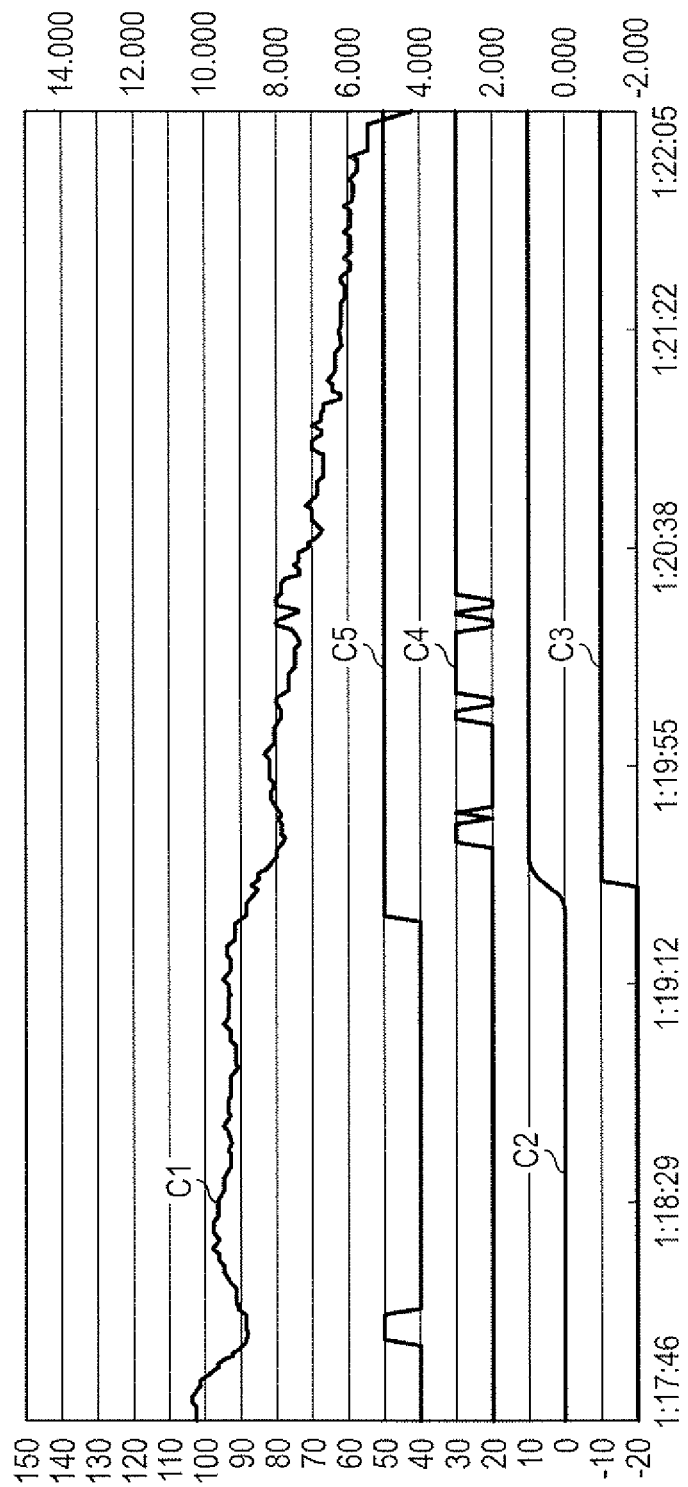
FIG. 12 is a view showing temporal changes of the biological signal, the state probability, and the generation of an alarm in the case where a process is performed in the second embodiment of the biological signal processing apparatus of the invention.

FIG. 12 shows an alarm generation in the second embodiment in the case where the blood pressure is rapidly lowered, and also a simple comparison in the related-art example with 80 mmHg (threshold), and a simple comparison with 90 mmHg (threshold). In the figure, C1 to C5 indicate changes of the same objects as those of FIG. 10. In the embodiment indicated by C3, a severe situation is determined rapidly as comparable as the simple comparison with 90 mmHg (threshold) which is indicated by C5, and an alarm generation control is performed. Unlike the simple comparison with 80 mmHg (threshold) which is indicated by C4, furthermore, the repetition of an alarm generation and a stop of an alarm generation is not observed, and it is seen that the state is stably detected.

Figure 13:
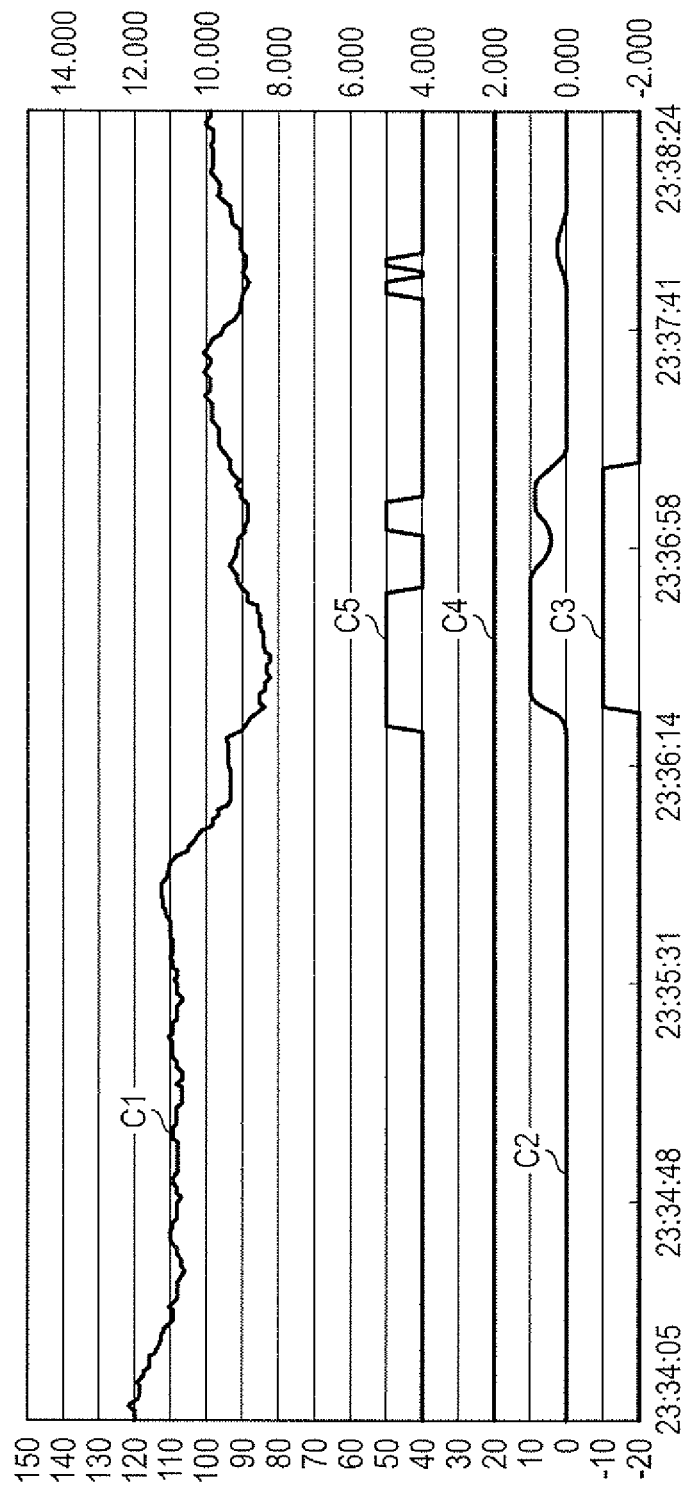
FIG. 13 is a view showing temporal changes of the biological signal, the state probability, and the generation of an alarm in the case where a process is performed in the second embodiment of the biological signal processing apparatus of the invention.
Figure 14:
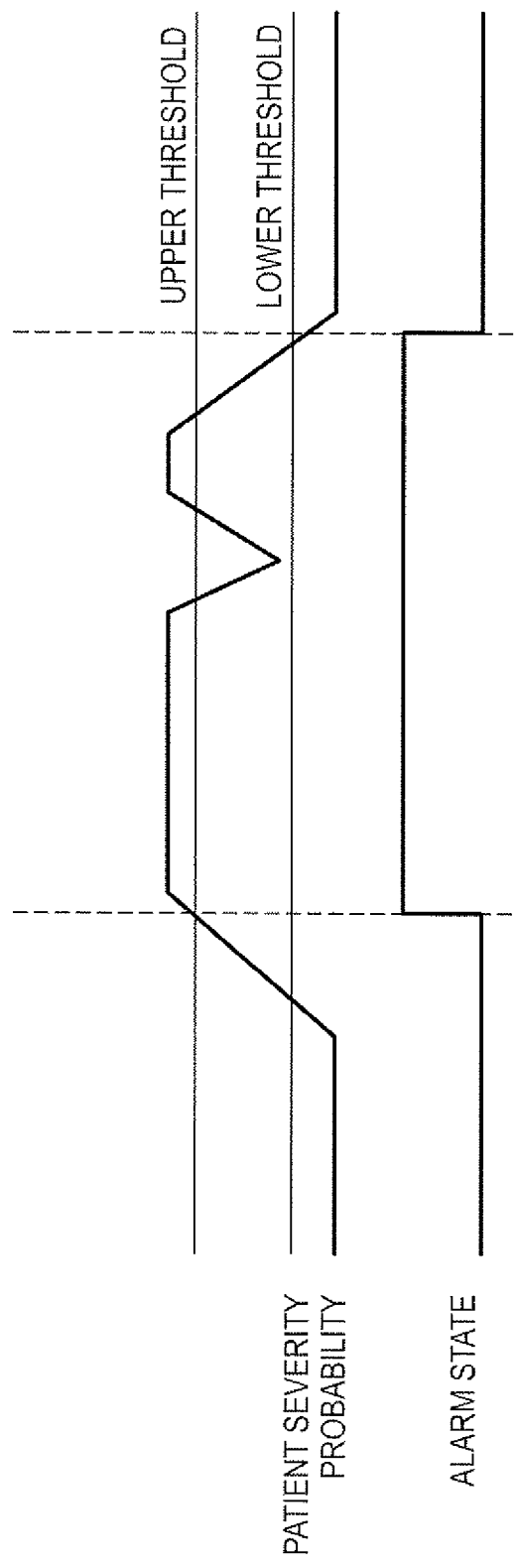
FIG. 14 is a view showing temporal changes illustrating effects due to upper and lower thresholds in the case where a process is performed in an embodiment of the biological signal processing apparatus of the invention.

FIG. 13 shows an operation in which, in a change of the severity determination probability in the embodiment, even when the probability is lowered, a period when a series of alarm generations is acquired because the threshold is configured by the upper and lower thresholds so that the determination is provided with hysteresis. In the figure, C1 to C5 indicate changes of the same objects as those of FIG. 10. Next, description will be made in detail. As shown in FIG. 14, when the severity determination probability once exceeds the upper threshold and an alarm is generated, the alarm generation is not stopped depending on the lowering of the probability which does not fall below the lower threshold, and therefore it is possible to eliminate the disadvantage in which an alarm generation and a stop of an alarm generation are frequently repeated.

Figure 15:
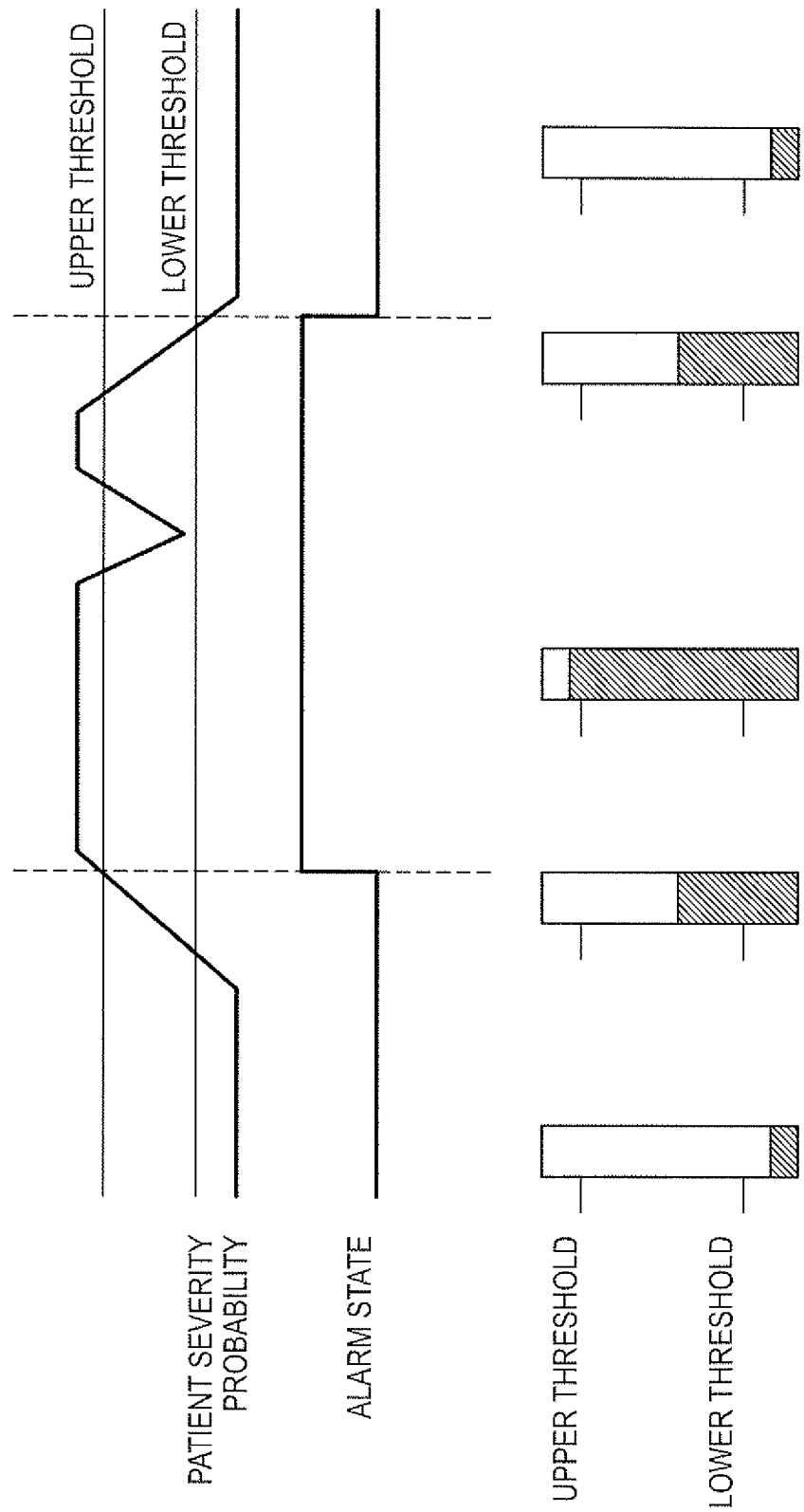
FIG. 15 is a view showing waveforms and bar graphs displayed in the case where a process due to the upper and lower thresholds is performed in an embodiment of the biological signal processing apparatus of the invention.

In the embodiments, the calculation controlling portion 30 controls the displaying device 52 so as to display the severity determination probability. In this case, the numerals of the severity determination probability, and a line graph corresponding to the numerals are displayed together with the time. As shown in FIG. 15, furthermore, a line graph which is to be displayed in an upper portion, an alarm state, and bar graphs (to be displayed in a lower portion) at appropriate timings are prepared, and then displayed. Therefore, it is possible to instinctively know the severity.

Figure 16:
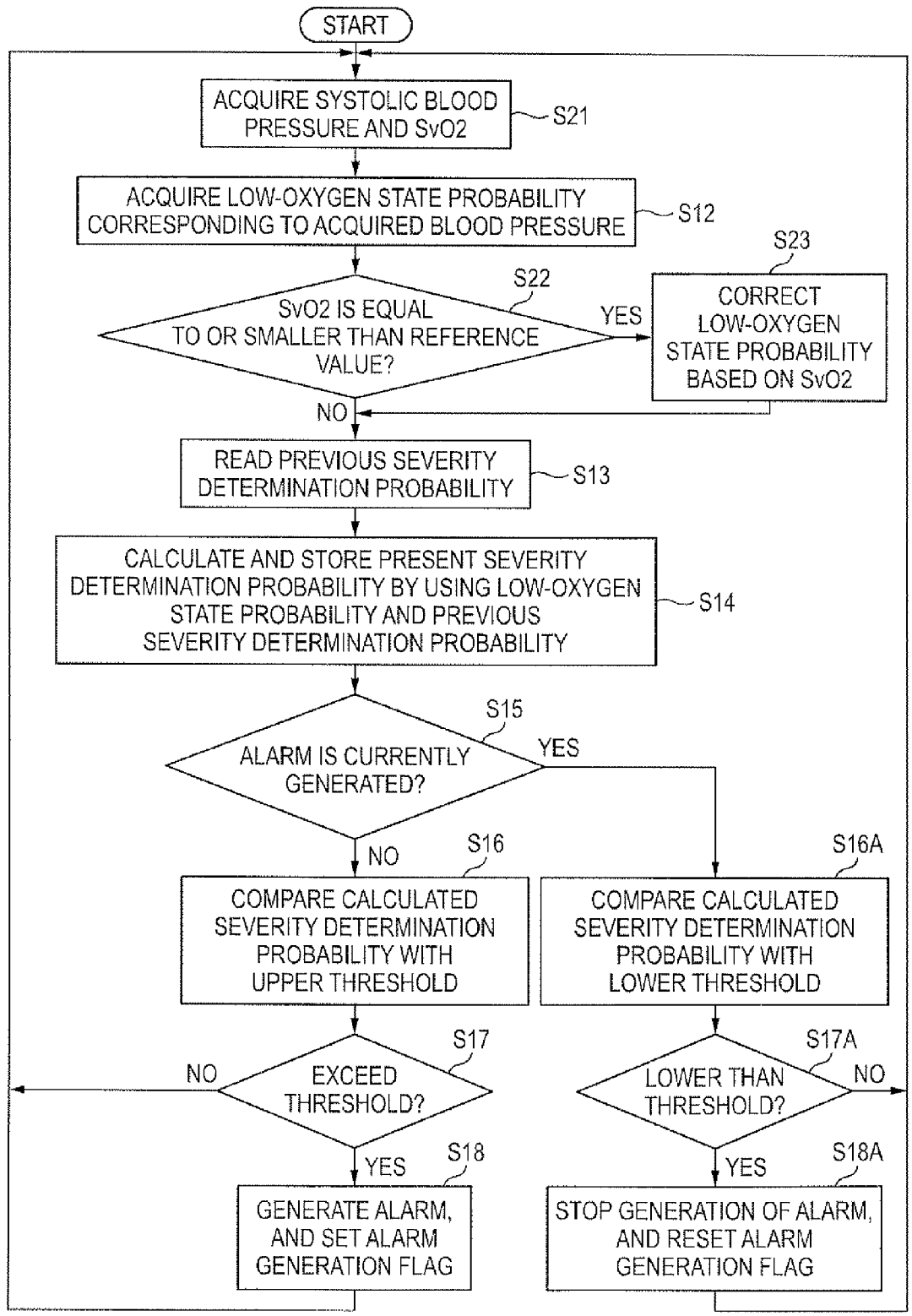
FIG. 16 is a flowchart showing the operation of a third embodiment of the biological signal processing apparatus of the invention.

FIG. 16 shows a flowchart of a process in a third embodiment which is an improvement of the second embodiment. In the embodiment, the low-oxygen state probability is corrected by the SvO2. In the case where the oxygen supply is insufficient for the demand, even when a small lowering of the blood pressure occurs, the patient severity is high, and hence it is requested to early generate an alarm. In a clinical site, the SvO2 is used as a parameter for monitoring the balance between the oxygen demand and the oxygen supply. The situation where the SvO2 is lowered means that the oxygen supply is insufficient for the oxygen demand of the full body.

The third embodiment includes a correcting unit which is not shown in FIG. 1, and which, when the SvO2 is equal to smaller than a reference value Sref %, corrects the low-blood pressure state probability Ps to be increased by Expression 2 below.

$$MODPs = Ps \times (Sref - SvO2)/k \qquad \text{Exp. 2}$$

In Expression 2, MODPs is corrected low-blood pressure state probability. In Expression 2, Sref and k are arbitrarily set in accordance with the degree of participation of multi-parameter. In the embodiment, Sref=60 and k=2 are employed. The embodiment in which the probability is corrected based on another biological signal of the same patient will be described. Alternatively, the correction may be performed by using the identical biological signal of the same patient. In the third embodiment, as shown in the flowchart of FIG. 16, the systolic blood pressure and the SvO2 are acquired in step S21. Subsequent to step S12 which is identical with that in FIG. 9, and the description of which is therefore omitted, then, it is determined whether the SvO2 is equal to or smaller than the reference value or not (S22). If YES, the corrected low-blood pressure state probability MODPs is acquired by Expression 2 above (S23). In step S14, in the case where the corrected low-blood pressure state probability MODPs has been acquired in step S23, this probability is used. The other processes are identical with those of the second embodiment.

Figures 17, 18:
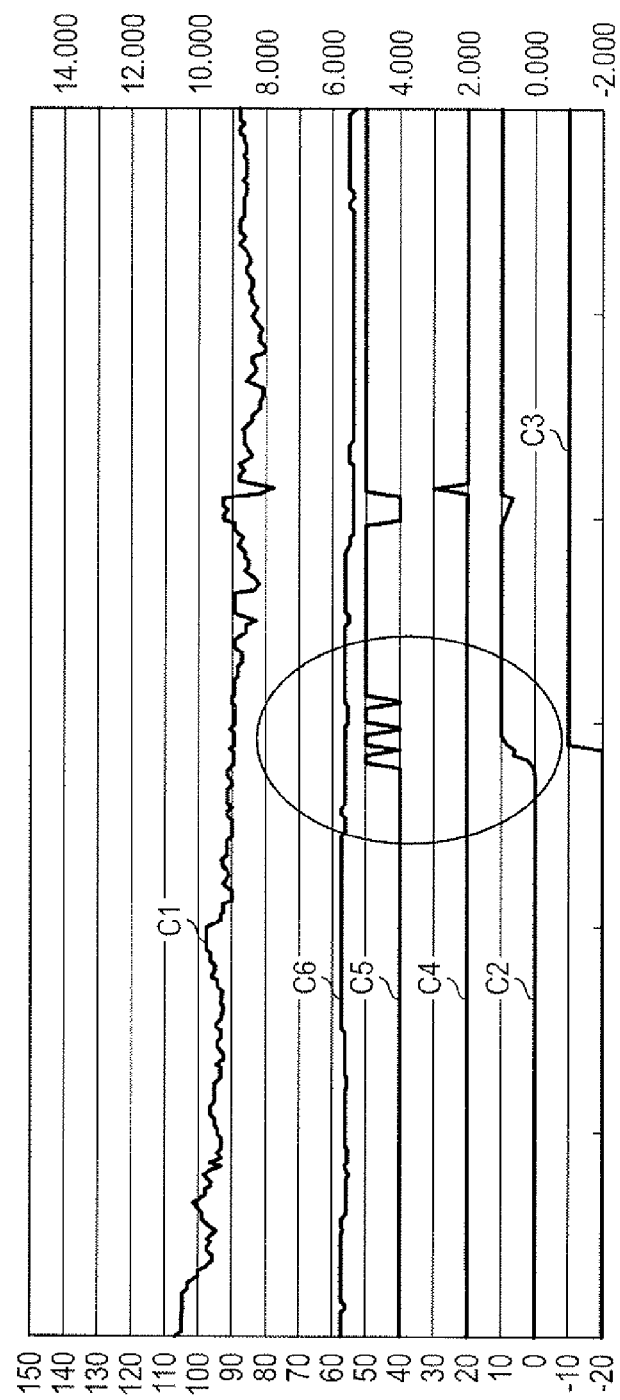
FIG. 17 is a view showing temporal changes of the biological signal, the state probability, and a generation of an alarm in the case where a process is performed in the third embodiment of the biological signal processing apparatus of the invention.
FIG. 18 is a view showing a comparison table of the state probability and the value of a biological signal used in a fourth embodiment of the biological signal processing apparatus of the invention.

FIG. 17 shows results in the case where the third embodiment is applied to the example of FIG. 10 which has been described. In the figure, C1 to C5 indicate changes of the same objects as those of FIG. 10, and C6 indicates a change of SvO2. In FIG. 17, it is seen that, as a result of the correction, the severity determination probability which is indicated by C2 is steeper than that in FIG. 10, and an alarm is early generated.

Figure 19:
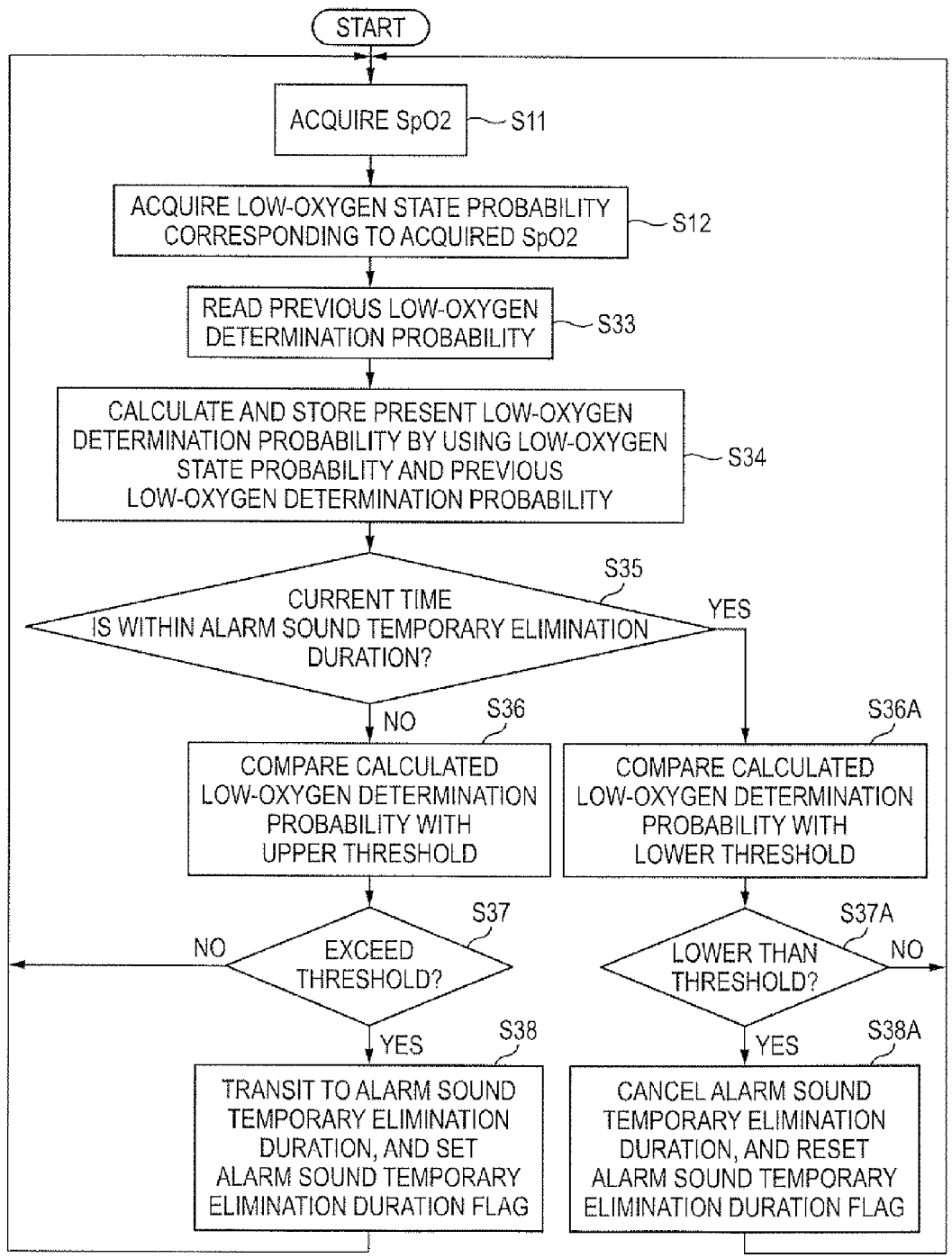
FIG. 19 is a flowchart showing the operation of the fourth embodiment of the biological signal processing apparatus of the invention.

Next, a fourth embodiment will be described. In the embodiment, the storage unit 31 stores a table in which, as shown in FIG. 18, the probability at which a low-oxygen state is produced (the low-oxygen state probability) and that at which a low-oxygen state is not produced are correlated with the value of the SpO2. The calculation controlling portion 30 performs processes based on the flowchart of FIG. 19.

Steps S11 and S12 are identical with those of the first embodiment. In the next step S33, the calculation controlling portion 30 reads the stored previous low-oxygen determination probability, calculates the present low-oxygen determination probability P(t), on the basis of Expression 1 above by using the low-oxygen state probability Ps which is obtained in step S12, and the previous low-oxygen determination probability P(t−1), and stores the calculated probability into a predetermined register (S34 (the determining unit 33)). Furthermore, the calculation controlling portion 30 checks the flag to determine whether the current time is within a temporary elimination duration of the alarm sound or not (S35).

If it is detected in step S35 that the current time is not within the temporary elimination duration of the alarm sound, the present low-oxygen determination probability P(t) is compared with the upper threshold (0.65) (S36) to detect whether the present low-oxygen determination probability P(t) exceeds the upper threshold (0.65) or not (S37). If it is detected that the present low-oxygen determination probability P(t) exceeds the upper threshold (0.65), the alarm generating device 51 is controlled so as to transit to the temporary elimination duration of the alarm sound, and an alarm sound temporary elimination duration flag is set (S38). Then, the control returns to step S11.

If it is detected in step S35 that the current time is within the temporary elimination duration of the alarm sound, the present low-oxygen determination probability P(t) is compared with the lower threshold (0.35) (S36A) to detect whether the present low-oxygen determination probability P(t) is smaller than the lower threshold (0.35) or not (S37A). If it is detected that the present low-oxygen determination probability P(t) is smaller than the lower threshold (0.35), the alarm generating device 51 is controlled so as to cancel the temporary elimination duration of the alarm sound, and the alarm sound temporary elimination duration flag is reset (S38A). Then, the control returns to step S11.

Figure 20:
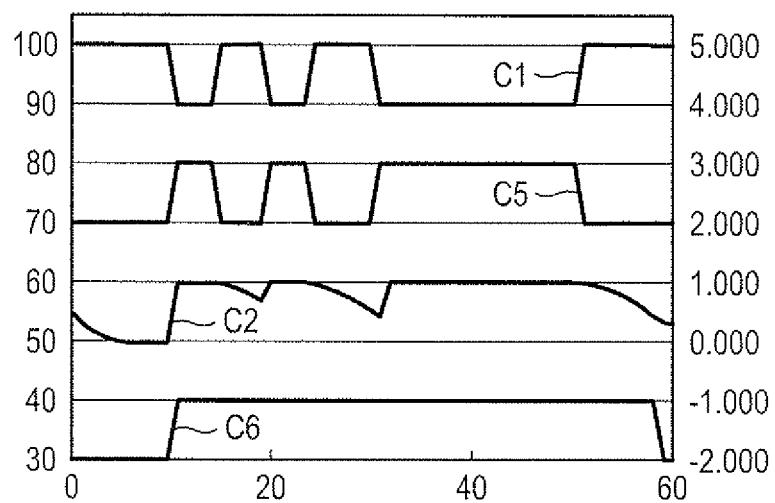
FIG. 20 is a view showing temporal changes of the biological signal, the state probability, and a alarm temporary elimination period in the case where a process is performed in the fourth embodiment of the biological signal processing apparatus of the invention.

As a result of the above-described process, in the case where the SpO2 (%) is measured as shown in FIG. 20, for example, the following process results are obtained in the embodiment. In a case such as that where the measured SpO2 (%) is intensely changed between 100% and 89%, the ON/OFF operation is correspondingly repeated in the simple comparison of the SpO2 with 90% (threshold) in the related art. When the low-oxygen determination probability P(t) is once set to 1, however, a change in which it becomes lower than the lower threshold (0.35) is hardly caused, and a series of alarm sound temporary elimination durations are continued. After a timing when the temporary stop switch of the operating portion 40 is operated, it is possible to avoid a cumbersome situation where the alarm sound temporary elimination is unintentionally cancelled. In FIG. 20, C1 indicates the SpO2 (%), C2 indicates the low-oxygen determination probability P(t), C5 indicates the simple comparison of the SpO2 with 90% (threshold), and C6 indicates the alarm sound temporary elimination duration.

Figure 21:
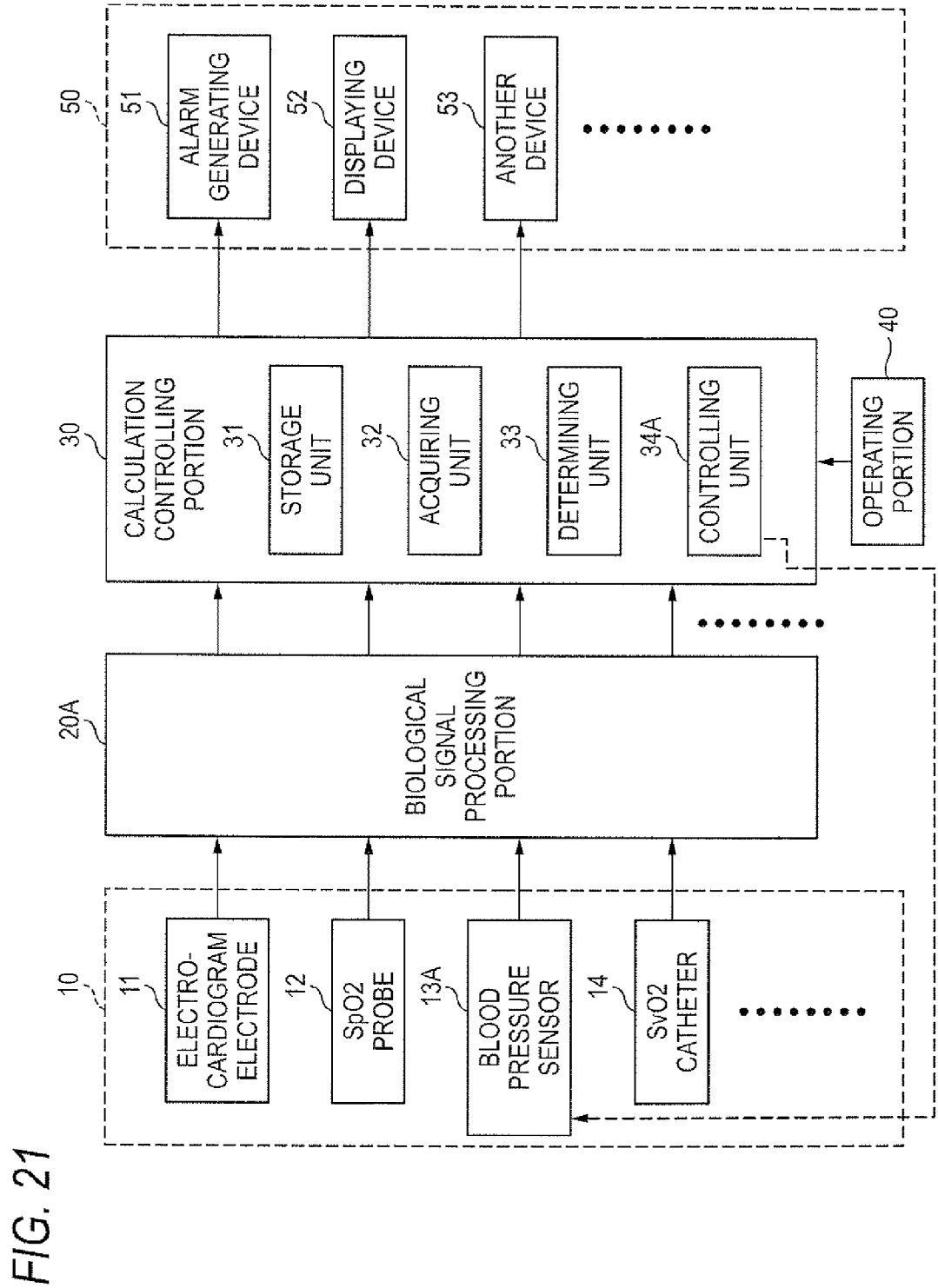
FIG. 21 is a diagram showing a fifth embodiment of the biological signal processing apparatus of the invention.

FIG. 21 is a diagram of a medical apparatus which is a fifth embodiment. In the medical apparatus, a blood pressure sensor 13A is a noninvasive blood pressure measuring apparatus which includes, for example, a cuff, a compressing pump, and an exhaust valve, and which is configured so that a controlling unit 34A of the calculation controlling portion 30 controls the compressing pump and the exhaust valve to control a noninvasive blood pressure measurement.

Figure 22:
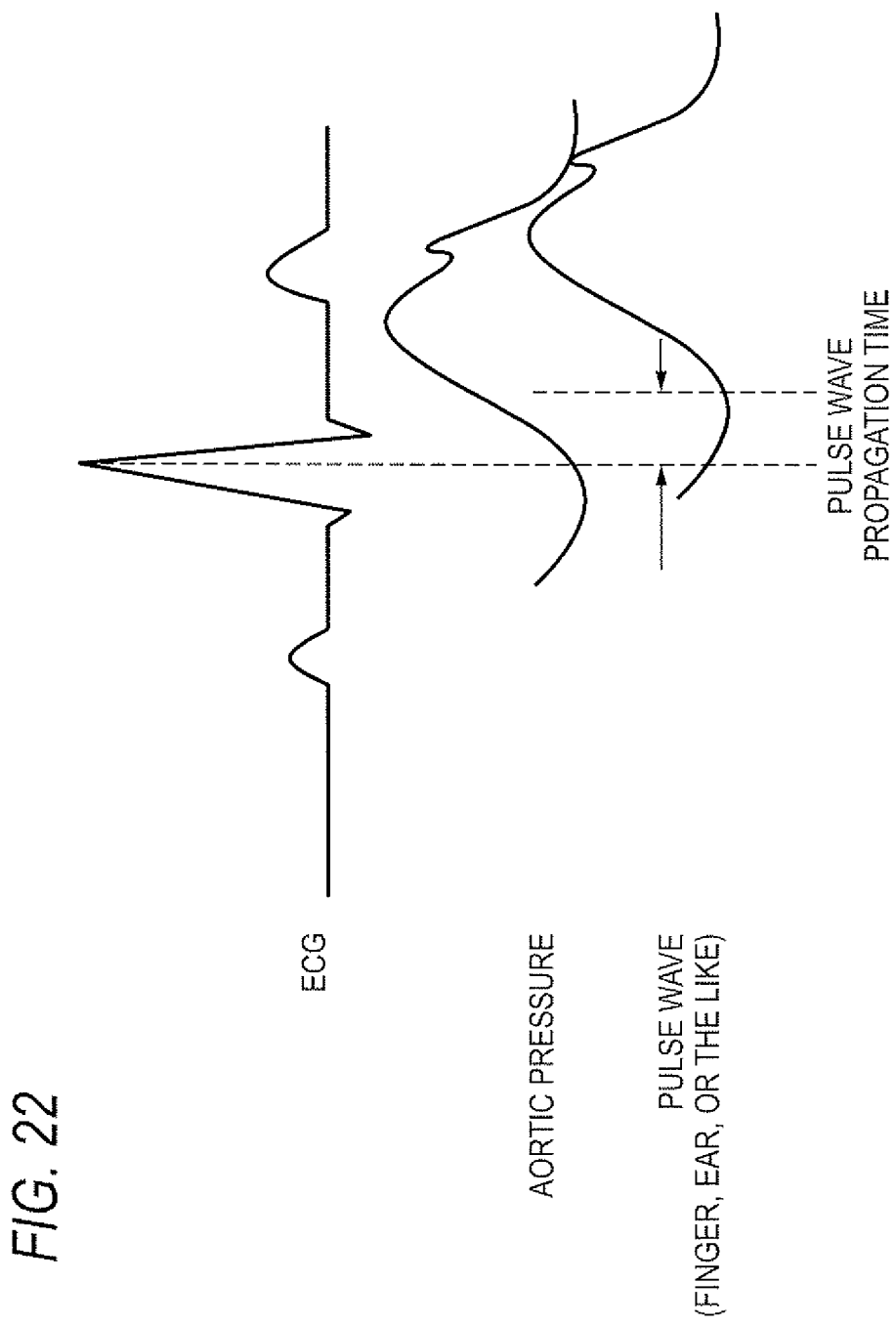
FIG. 22 is a waveform chart illustrating the pulse wave transit time.

A biological signal processing portion 20A acquires the pulse wave transit time based on an ECG signal acquired from ECG electrodes 11, and a pulse wave acquired from the SpO2 probe 12, and estimates the blood pressure based on them. Specifically, as shown in FIG. 22, a specific point of a pulse wave on the side of peripheral blood vessels such as a finger or an ear appears with a time lag with respect to a specific point of an aortic pulse wave. This time lag is the pulse wave transit time. In the case where different blood pressures appear, for example, at rest and in exercise, the blood pressure and the pulse wave transit time are measured, and a specific constant inherent in the subject is obtained. Thereafter, the blood pressure can be estimated simply by measuring the pulse wave transit time (in detail, refer to JP-A-7-313472). In order to use this technique, the specific constant is set in the calculation controlling portion 30.

The storage unit 31 includes a table in which, as shown in FIG. 23, a blood pressure variation state probability of from 0 to 1.0 is correlated in steps of 0.05 with from 90 mmHg to 70 mmHg. The upper and lower thresholds are set to 0.65 and 0.35, respectively.

Figure 24:
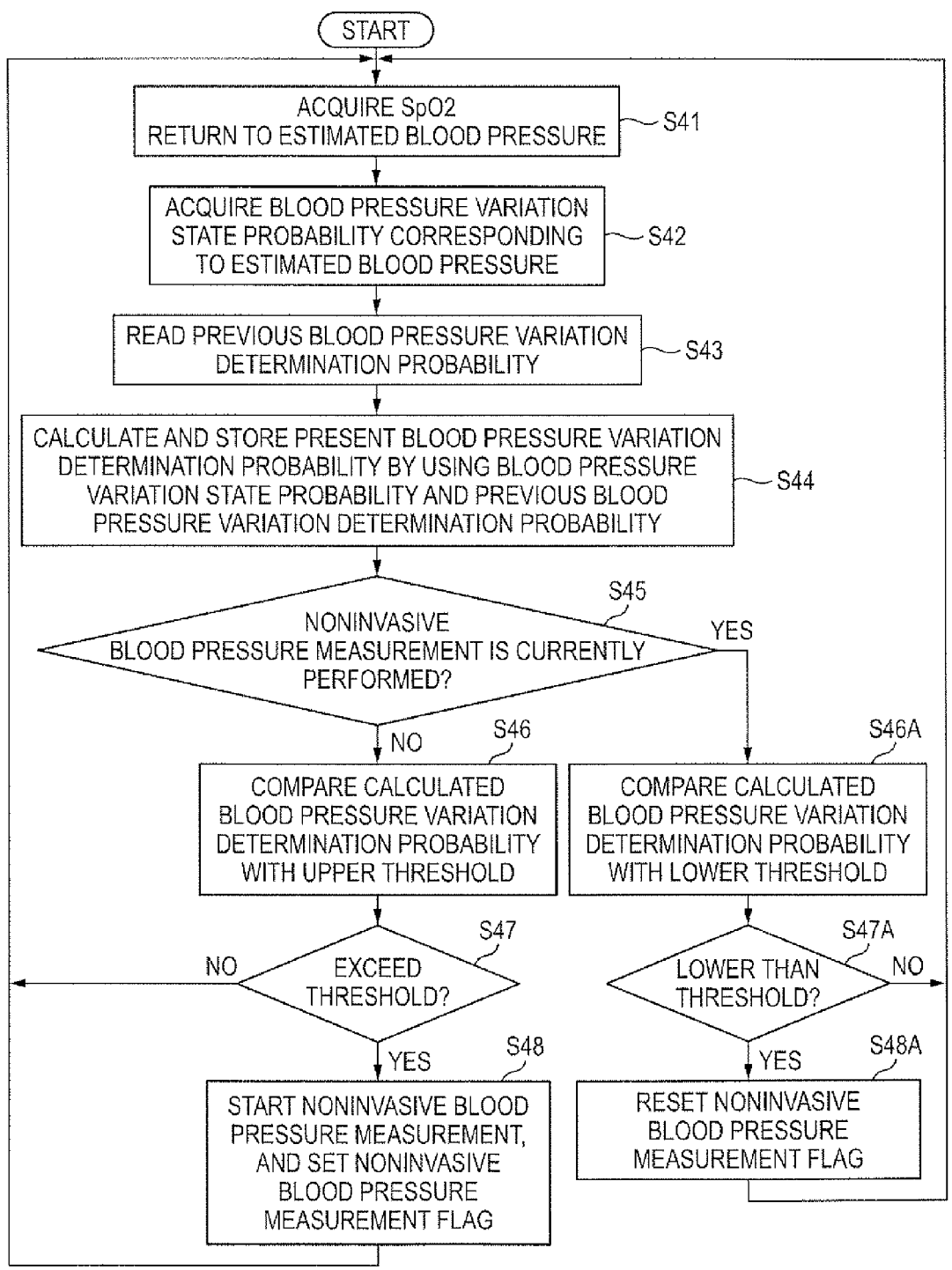
FIG. 24 is a flowchart showing the operation of the fifth embodiment of the biological signal processing apparatus of the invention.

The calculation controlling portion 30 operates in accordance with the flowchart shown in FIG. 24. The SpO2 is acquired as a biological signal, and then converted to an estimated blood pressure in the biological signal processing portion 20A (S41). The calculation controlling portion 30 acquires the converted blood pressure, and acquires the corresponding blood pressure variation state probability from the table which is stored in the storage unit 31, and which is shown in FIG. 23 (S42 (the acquiring unit 32)).

Then, the calculation controlling portion 30 reads the stored previous blood pressure variation determination probability (S43), calculates the present blood pressure variation determination probability P(t), on the basis of Expression 1 above by using the blood pressure variation state probability Ps which is acquired in step S42, and the previous blood pressure variation determination probability P(t−1), and stores the calculated probability in a predetermined register (S44 (the determining unit 33)). Furthermore, the calculation controlling portion 30 checks the flag to determine whether a noninvasive blood pressure measurement is currently performed or not (S45).

If it is detected in step S45 that a noninvasive blood pressure measurement is not currently performed, the present blood pressure variation determination probability P(t) is compared with the upper threshold (0.65) (S46). In the comparison of step S46, it is checked whether the present blood pressure variation determination probability P(t) exceeds the upper threshold (0.65) or not (S47). If determined YES, the blood pressure sensor 13A is controlled so as to perform a noninvasive blood pressure measurement, and a measurement flag is set (S48). Then, the control returns to step S41. The steps following step S41 are repeated every one sampling.

If it is detected in step S45 that a noninvasive blood pressure measurement is currently performed, the present blood pressure variation determination probability P(t) is compared with the lower threshold (0.35) (S46A). In the comparison of step S46A, it is checked whether the present blood pressure variation determination probability P(t) is smaller than the lower threshold (0.35) or not (S47A). If determined YES, the measurement flag is reset (S48A). Then, the control returns to step S41. Also in the case where the control is branched in step S47 to NO, the steps following step S41 are repeated every one sampling.

Figure 25:
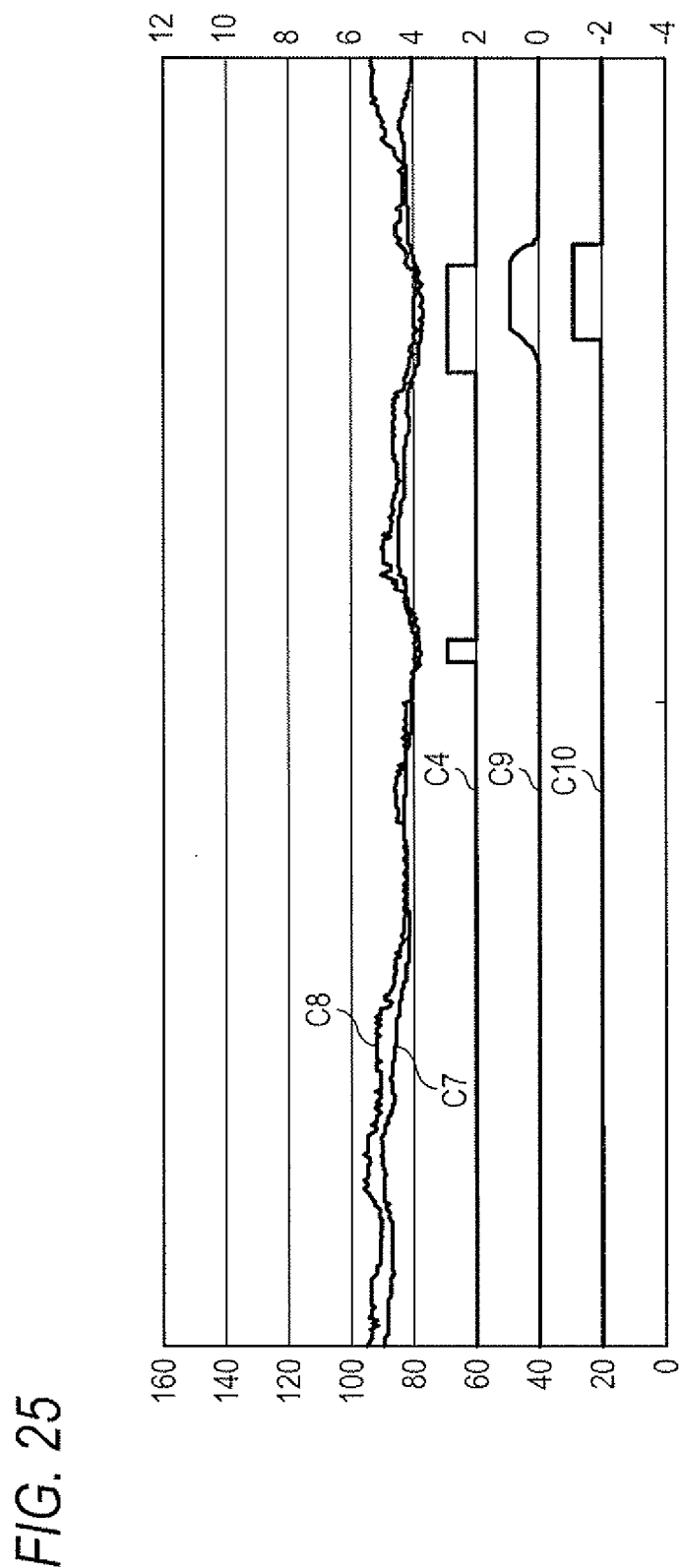
FIG. 25 is a view showing temporal changes of the biological signal, the state probability, and a non-invasive blood pressure measurement start corresponding signal in the case where a process is performed in the fifth embodiment of the biological signal processing apparatus of the invention.

In the thus configured medical apparatus of the fifth embodiment, for example, it is assumed that, as shown in FIG. 25, the estimated blood pressure indicated by C7 is changed and the invasive blood pressure which is indicated by C8 for reference is changed. In this case, in the portion where the blood pressure is lowered to be lower than 80 mmHg or less at the first time, the blood pressure variation state probability Ps is 1, but the blood pressure variation determination probability P(t) indicated by C9 does not exceed the upper threshold (0.65). In the simple comparison of the estimated blood pressure with 80 mmHg (threshold) which is indicated by C4, therefore, a trigger for starting a noninvasive blood pressure measurement is produced. In the medical apparatus of the fifth embodiment, by contrast, such a trigger is not produced, which is indicated by C10.

Next, in the portion where the blood pressure is lowered to retain in the vicinity of 80 mmHg or less at the second time, the blood pressure variation state probability Ps is continued to be 1, and the blood pressure variation determination probability P(t) exceeds the upper threshold (0.65). In the simple comparison of the estimated blood pressure with 80 mmHg (threshold) which is indicated by C4, therefore, a trigger for starting a noninvasive blood pressure measurement is produced. In the medical apparatus of the fifth embodiment which is indicated by C10, next, it is determined that the blood pressure variation determination probability P(t) exceeds the upper threshold (0.65), and a trigger is generated at a timing when the blood pressure is surely varied and the blood pressure measurement is indispensable. When after a while the blood pressure variation determination probability P(t) becomes smaller than the lower threshold (0.35), the measurement flag for the noninvasive blood pressure measurement is reset, and the determination whether the next noninvasive blood pressure measurement is started or not is performed on the basis of the blood pressure variation determination probability P(t).

According to the fifth embodiment, namely, an unwanted trigger generation subjected to a short-time measurement variation in which a noninvasive blood pressure measurement is not necessary, or that due to noises based on influences such as a body motion of the patient can be suppressed, and a trigger generation for an adequate measurement start can be ensured.

In the embodiments, as a unit for providing the state probability corresponding to, in advance, each value of a biological signal divided into a predetermined width, the comparison table in which the state probability of the living body state and the values of the biological signal correspond to each other in advance is used. Alternatively, the unit for providing the state probability may be formed by a configuration where a biological signal is deemed as a continuous vale and the state probability is provided each time based on calculation.

According to an aspect of the invention, state probability corresponding to, in advance, each value of a biological signal is provided, a biological signal is acquired in time series from a living body, state probability corresponding to the value of the biological signal is acquired based on the provided state probability, a determination probability is acquired at which it is determined whether a predetermined process performed or not, based on the state probability which is acquired in time series, and a determination is performed by using the determination probability. Therefore, a determination which is dazzled by an instantaneous change of a biological signal or the like can be eliminated, and a determination and a control can be adequately performed in the case where a predetermined process such as that of generating an alarm on the basis of a biological signal is performed.

According to an aspect of the invention, with respect to the process and control of generating an alarm, those of returning from the alarm temporary eliminated state, and those of determining whether the process of acquiring the second biological signal by using the first biological signal is started or not, a determination and control which are dazzled by an instantaneous change of a biological signal or the like can be eliminated, and a determination and a control can be adequately performed.

According to an aspect of the invention, the determination probability is displayed on the displaying unit, and hence it is possible to instinctively know the living body state while viewing the determination probability acquired from the state probability of the living body state, in place of the biological signal.

What is claimed is:

1. A biological signal processing apparatus comprising:
a calculation controller which controls a process of generating an alarm, and which comprises:
a provider which provides state probability based upon one of: a state probability table in which the state probability corresponds to, in advance, a value of a first biological signal; and a calculation based on a deemed continuous value based on a measured first biological signal;
an acquirer which acquires a first biological signal in time series from a living body, and which acquires, from the provider, state probability in time series that corresponds to a value of the acquired first biological signal in time series; and
a determiner which calculates, by using a recurrence expression, present determination probability based on: present state probability acquired by the acquirer; and past determination probability, and which performs a determination whether a process is performed or not using the present determination probability, wherein
the calculation controller determines whether the alarm is currently on or not,
when it is determined that the alarm is not currently on, (i) the determiner compares the calculated present determination probability with a first threshold to determine whether a process of generating an alarm is performed or not, and (ii) when the determiner determines to generate the alarm, the calculation controller initiates generation of the alarm and an alarm generation flag is set; and
when it is determined that the alarm is currently on, (i) the determiner compares the calculated present determination probability with a second threshold to determine whether a process of stopping the alarm is performed or not, and (ii) when the determiner determines to stop the alarm, the calculation controller initiates stoppage of the alarm and the alarm generation flag is reset.

2. The biological signal processing apparatus according to claim 1, wherein the first threshold is an upper threshold and the second threshold is a lower threshold, and the determiner performs the determination with hysteresis by using the upper threshold and the lower threshold.

3. The biological signal processing apparatus according to claim 1, wherein the determiner calculates the determination probability based on Bayes's theorem.

4. The biological signal processing apparatus according to claim 1, further comprising: a display; and a display controller which displays the determination probability acquired by the determiner on the display.

5. The biological signal processing apparatus according to claim 1, further comprising: a corrector which corrects the state probability acquired by the acquirer based on a second biological signal which is identical with or different from the first biological signal.

6. A method of controlling a medical apparatus, the method comprising:
acquiring a first biological signal in time series from a living body, and acquiring state probability in time series that corresponds to a value of the acquired first biological signal in time series, based upon one of: a state probability table in which the state probability corresponds to, in advance, a value of a first biological signal; and a calculation based on a deemed continuous value based on a measured first biological signal;
calculating, by using a recurrence expression, present determination probability based on: present state probability of the acquired state probability; and past determination probability;
determining whether an alarm is currently on or not;
when it is determined that the alarm is not currently on, (i) comparing the calculated present determination probability with a first threshold to determine whether a process of generating an alarm is performed or not and (ii) when it is determined to generate the alarm, initiating generation of the alarm and setting an alarm generation flag; and
when it is determined that the alarm is currently on, (i) comparing the calculated present determination probability with a second threshold to determine whether a process of stopping the alarm is performed or not and (ii) when it is determined to stop the alarm, initiating stoppage of the alarm and resetting the alarm generation flag.

7. The method according to claim 6, wherein the first threshold is an upper threshold and the second threshold is a lower threshold, and hysteresis including the upper threshold and the lower threshold is used.

8. The method according to claim 6, wherein the determination probability is calculated based on Bayes's theorem.

9. The method according to claim 6, further comprising: displaying the determination probability.

10. The method according to claim 6, further comprising: correcting the acquired state probability based on a second biological signal which is identical with or different from the first biological signal.

* * * * *